(12) United States Patent
Hartig

(10) Patent No.: US 11,786,191 B2
(45) Date of Patent: Oct. 17, 2023

(54) CONTRAST-ENHANCED TOMOSYNTHESIS WITH A COPPER FILTER

(71) Applicant: Hologic, Inc., Marlborough, MA (US)

(72) Inventor: Helmut Hartig, Weisskirchen (AT)

(73) Assignee: Hologic, Inc., Marlborough, MA (US)

( * ) Notice: Subject to any disclaimer, the term of this patent is extended or adjusted under 35 U.S.C. 154(b) by 214 days.

(21) Appl. No.: 17/322,329

(22) Filed: May 17, 2021

(65) Prior Publication Data
US 2022/0361831 A1 Nov. 17, 2022

(51) Int. Cl.
*A61B 6/00* (2006.01)
*A61B 6/02* (2006.01)
*A61B 6/04* (2006.01)

(52) U.S. Cl.
CPC ............ *A61B 6/4035* (2013.01); *A61B 6/025* (2013.01); *A61B 6/0414* (2013.01); *A61B 6/4452* (2013.01); *A61B 6/461* (2013.01); *A61B 6/502* (2013.01)

(58) Field of Classification Search
CPC ...... A61B 6/025; A61B 6/0414; A61B 6/4035
USPC .......................................................... 600/431
See application file for complete search history.

(56) References Cited

U.S. PATENT DOCUMENTS

| | | |
|---|---|---|
| 3,365,575 A | 1/1968 | Strax |
| 3,502,878 A | 3/1970 | Stewart |
| 3,863,073 A | 1/1975 | Wagner |
| 3,971,950 A | 7/1976 | Evans et al. |
| 4,160,906 A | 7/1979 | Daniels et al. |
| 4,212,306 A | 7/1980 | Mahmud |
| 4,310,766 A | 1/1982 | Finkenzeller et al. |
| 4,380,086 A | 4/1983 | Vagi |
| 4,496,557 A | 1/1985 | Malen et al. |
| 4,513,433 A | 4/1985 | Weiss et al. |
| 4,542,521 A | 9/1985 | Hahn et al. |

(Continued)

FOREIGN PATENT DOCUMENTS

| | | |
|---|---|---|
| CN | 102222594 | 10/2011 |
| CN | 105286904 | 2/2016 |

(Continued)

OTHER PUBLICATIONS

"Essentials for life: Senographe Essential Full-Field Digital Mammography system", GE Health-care Brochure, MM-0132-05.06-EN-US, 2006, 12 pgs.

(Continued)

*Primary Examiner* — Boniface Ngathi
(74) *Attorney, Agent, or Firm* — Merchant & Gould P.C.

(57) ABSTRACT

Systems and methods for tomosynthesis with an x-ray filter are disclosed. The present technology provides performing breast tomosynthesis in the presence of an x-ray filter. For example, an x-ray filter may be placed between an x-ray source and breast tissue. The filter may proportionally filter out a subset of the energies emitted by the x-ray source. A filter may include characteristics to filter x-ray energies based on a k-edge of a contrast agent introduced into the breast, such that the breast tissue has relatively greater exposure to x-ray energies above the k-edge of the contrast agent to illuminate the contrast agent without substantial illumination of other breast tissue. Thus, tomosynthesis (Continued)

images similar to those obtained using subtraction may be acquired without software-based contrast enhancing techniques.

10 Claims, 8 Drawing Sheets

(56) References Cited

U.S. PATENT DOCUMENTS

| | | |
|---|---|---|
| 4,559,641 A | 12/1985 | Caugant et al. |
| 4,658,409 A | 4/1987 | Summ |
| 4,662,379 A | 5/1987 | Macovski |
| 4,706,269 A | 11/1987 | Reina et al. |
| 4,721,856 A | 1/1988 | Saotome et al. |
| 4,744,099 A | 5/1988 | Huettenrauch et al. |
| 4,752,948 A | 6/1988 | MacMahon |
| 4,760,589 A | 7/1988 | Siczek |
| 4,763,343 A | 8/1988 | Yanaki |
| 4,773,086 A | 9/1988 | Fujita et al. |
| 4,773,087 A | 9/1988 | Plewes |
| 4,819,258 A | 4/1989 | Kleinman et al. |
| 4,821,727 A | 4/1989 | Levene et al. |
| 4,969,174 A | 11/1990 | Scheid et al. |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,163,075 A | 11/1992 | Lubinsky et al. |
| 5,164,976 A | 11/1992 | Scheid et al. |
| 5,199,056 A | 3/1993 | Darrah |
| 5,212,637 A | 5/1993 | Saxena |
| 5,240,011 A | 8/1993 | Assa |
| 5,256,370 A | 10/1993 | Slattery |
| 5,274,690 A | 12/1993 | Burke |
| 5,289,520 A | 2/1994 | Pellegrino et al. |
| 5,291,539 A | 3/1994 | Thumann et al. |
| 5,313,510 A | 5/1994 | Ebersberger |
| 5,359,637 A | 10/1994 | Webber |
| 5,365,562 A | 11/1994 | Toker |
| 5,415,169 A | 5/1995 | Siczek et al. |
| 5,426,685 A | 6/1995 | Pellegrino et al. |
| 5,452,367 A | 9/1995 | Bick et al. |
| 5,506,877 A | 4/1996 | Niklason et al. |
| 5,526,394 A | 6/1996 | Siczek et al. |
| 5,528,658 A | 6/1996 | Hell |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzke et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,844 A | 9/1997 | Webber |
| 5,668,889 A | 9/1997 | Hara |
| 5,706,327 A | 1/1998 | Adamkowski et al. |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,841,829 A | 11/1998 | Dolazza |
| 5,844,965 A | 12/1998 | Galkin |
| 5,864,146 A | 1/1999 | Karellas |
| 5,872,828 A | 2/1999 | Niklason et al. |
| 5,878,104 A | 3/1999 | Ploetz |
| 5,896,437 A | 4/1999 | Ploetz |
| 5,941,832 A | 8/1999 | Tumey et al. |
| 5,970,118 A | 10/1999 | Sokolov |
| 5,983,123 A | 11/1999 | Shmulewitz |
| 5,986,662 A | 11/1999 | Argiro et al. |
| 5,999,836 A | 12/1999 | Nelson et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,167,115 A | 12/2000 | Inoue |
| 6,175,117 B1 | 1/2001 | Komardin et al. |
| 6,196,715 B1 | 3/2001 | Nambu et al. |
| 6,207,958 B1 | 3/2001 | Giakos |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,244,507 B1 | 6/2001 | Garland |
| 6,256,369 B1 | 7/2001 | Lai |
| 6,256,370 B1 | 7/2001 | Yavuz |
| 6,272,207 B1 | 8/2001 | Tang |
| 6,289,235 B1 | 9/2001 | Webber et al. |
| 6,292,530 B1 | 9/2001 | Yavus et al. |
| 6,327,336 B1 | 12/2001 | Gingold et al. |
| 6,341,156 B1 | 1/2002 | Baetz et al. |
| 6,345,194 B1 | 2/2002 | Nelson et al. |
| 6,375,352 B1 | 4/2002 | Hewes et al. |
| 6,411,836 B1 | 6/2002 | Patel et al. |
| 6,415,015 B2 | 7/2002 | Nicolas et al. |
| 6,418,189 B1 | 7/2002 | Schafer |
| 6,442,288 B1 | 8/2002 | Haerer et al. |
| 6,459,925 B1 | 10/2002 | Nields et al. |
| 6,480,565 B1 | 11/2002 | Ning |
| 6,490,476 B1 | 12/2002 | Townsend et al. |
| 6,501,819 B2 | 12/2002 | Unger et al. |
| 6,542,575 B1 | 4/2003 | Schubert |
| 6,553,096 B1 | 4/2003 | Zhou et al. |
| 6,556,655 B1 | 4/2003 | Chichereau et al. |
| 6,574,304 B1 | 6/2003 | Hsieh et al. |
| 6,574,629 B1 | 6/2003 | Cooke, Jr. et al. |
| 6,597,762 B1 | 7/2003 | Ferrant et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol et al. |
| 6,751,285 B2 | 6/2004 | Eberhard et al. |
| 6,758,824 B1 | 7/2004 | Miller et al. |
| 6,813,334 B2 | 11/2004 | Koppe et al. |
| 6,882,700 B2 | 4/2005 | Wang et al. |
| 6,885,724 B2 | 4/2005 | Li et al. |
| 6,895,076 B2 | 5/2005 | Halsmer |
| 6,909,790 B2 | 6/2005 | Tumey et al. |
| 6,909,792 B1 | 6/2005 | Carrott et al. |
| 6,912,319 B1 | 6/2005 | Barnes et al. |
| 6,940,943 B2 | 9/2005 | Claus et al. |
| 6,950,493 B2 | 9/2005 | Besson |
| 6,957,099 B1 | 10/2005 | Arnone et al. |
| 6,970,531 B2 | 11/2005 | Eberhard et al. |
| 6,978,040 B2 | 12/2005 | Berestov |
| 6,987,831 B2 | 1/2006 | Ning |
| 6,999,554 B2 | 2/2006 | Mertelmeier |
| 7,001,071 B2 | 2/2006 | Deuringer |
| 7,016,461 B2 | 3/2006 | Rotondo |
| 7,110,490 B2 | 9/2006 | Eberhard et al. |
| 7,110,502 B2 | 9/2006 | Tsuji |
| 7,116,749 B2 | 10/2006 | Besson |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,190,758 B2 | 3/2007 | Hagiwara |
| 7,206,462 B1 | 4/2007 | Betke |
| 7,244,063 B2 | 7/2007 | Eberhard |
| 7,245,694 B2 | 7/2007 | Jing et al. |
| 7,286,645 B2 | 10/2007 | Freudenberger |
| 7,302,031 B2 | 11/2007 | Hjam et al. |
| 7,315,607 B2 | 1/2008 | Ramsauer |
| 7,319,735 B2 | 1/2008 | Defreitas et al. |

(56) References Cited

U.S. PATENT DOCUMENTS

| | | |
|---|---|---|
| 7,319,736 B2 | 1/2008 | Rotondo |
| 7,323,692 B2 | 1/2008 | Rowlands et al. |
| 7,331,264 B2 | 2/2008 | Ozawa |
| 7,430,272 B2 | 9/2008 | Jing et al. |
| 7,443,949 B2 | 10/2008 | Defreitas et al. |
| 7,577,282 B2 | 8/2009 | Gkanatsios et al. |
| 7,583,786 B2 | 9/2009 | Jing et al. |
| 7,609,806 B2 | 10/2009 | Defreitas et al. |
| 7,616,731 B2 | 11/2009 | Pack |
| 7,616,801 B2 | 11/2009 | Gkanatsios et al. |
| 7,630,531 B2 | 12/2009 | Chui |
| 7,630,533 B2 | 12/2009 | Ruth et al. |
| 7,688,940 B2 | 3/2010 | Defreitas et al. |
| 7,697,660 B2 | 4/2010 | Ning |
| 7,702,142 B2 | 4/2010 | Ren et al. |
| 7,760,853 B2 | 7/2010 | Jing et al. |
| 7,760,924 B2 | 7/2010 | Ruth et al. |
| 7,792,245 B2 | 9/2010 | Hitzke et al. |
| 7,831,296 B2 | 11/2010 | Defreitas et al. |
| 7,839,979 B2 | 11/2010 | Hauttmann |
| 7,869,563 B2 | 1/2011 | Defreitas et al. |
| 7,881,428 B2 | 2/2011 | Jing et al. |
| 7,885,384 B2 | 2/2011 | Mannar |
| 7,894,646 B2 | 2/2011 | Shirahata et al. |
| 7,916,915 B2 | 3/2011 | Gkanatsios et al. |
| 7,949,091 B2 | 5/2011 | Jing et al. |
| 7,986,765 B2 | 7/2011 | Defreitas et al. |
| 7,991,106 B2 | 8/2011 | Ren et al. |
| 8,031,834 B2 | 10/2011 | Ludwig |
| 8,131,049 B2 | 3/2012 | Ruth et al. |
| 8,155,421 B2 | 4/2012 | Ren et al. |
| 8,170,320 B2 | 5/2012 | Smith et al. |
| 8,175,219 B2 | 5/2012 | Defreitas et al. |
| 8,285,020 B2 | 10/2012 | Gkanatsios et al. |
| 8,416,915 B2 | 4/2013 | Jing et al. |
| 8,452,379 B2 | 5/2013 | DeFreitas et al. |
| 8,457,282 B2 | 6/2013 | Baorui et al. |
| 8,515,005 B2 | 8/2013 | Ren et al. |
| 8,559,595 B2 | 10/2013 | Defreitas et al. |
| 8,565,372 B2 | 10/2013 | Stein et al. |
| 8,565,374 B2 | 10/2013 | DeFreitas et al. |
| 8,565,860 B2 | 10/2013 | Kimchy |
| 8,571,289 B2 | 10/2013 | Ruth et al. |
| 8,712,127 B2 | 4/2014 | Ren et al. |
| 8,767,911 B2 | 7/2014 | Ren et al. |
| 8,787,522 B2 | 7/2014 | Smith et al. |
| 8,824,752 B1 | 9/2014 | Fonte |
| 8,831,171 B2 | 9/2014 | Jing et al. |
| 8,853,635 B2 | 10/2014 | O'Connor |
| 8,873,716 B2 | 10/2014 | Ren et al. |
| 9,020,579 B2 | 4/2015 | Smith |
| 9,042,612 B2 | 5/2015 | Gkanatsios et al. |
| 9,066,706 B2 | 6/2015 | Defreitas et al. |
| 9,226,721 B2 | 1/2016 | Ren et al. |
| 9,460,508 B2 | 10/2016 | Gkanatsios et al. |
| 9,498,175 B2 | 11/2016 | Stein et al. |
| 9,498,180 B2 | 11/2016 | Ren |
| 9,502,148 B2 | 11/2016 | Ren |
| 9,549,709 B2 | 1/2017 | DeFreitas et al. |
| 9,851,888 B2 | 12/2017 | Gkanatsios et al. |
| 9,895,115 B2 | 2/2018 | Ren |
| 10,108,329 B2 | 10/2018 | Gkanatsios et al. |
| 10,194,875 B2 | 2/2019 | DeFreitas et al. |
| 10,296,199 B2 | 5/2019 | Gkanatsios |
| 10,413,255 B2 | 9/2019 | Stein |
| 10,452,252 B2 | 10/2019 | Gkanatsios et al. |
| 10,638,994 B2 | 5/2020 | DeFreitas |
| 10,719,223 B2 | 7/2020 | Gkanatsios |
| 10,881,359 B2 | 1/2021 | Williams |
| 10,905,385 B2 | 2/2021 | DeFreitas |
| 10,959,694 B2 | 3/2021 | Jing et al. |
| 11,076,820 B2 | 8/2021 | Smith |
| 11,090,017 B2 | 8/2021 | Zhang |
| 11,096,644 B2 | 8/2021 | DeFreitas |
| 2001/0038681 A1 | 11/2001 | Stanton et al. |
| 2002/0012450 A1 | 1/2002 | Tsujii |
| 2002/0048343 A1 | 4/2002 | Launay et al. |
| 2002/0050986 A1 | 5/2002 | Inouc et al. |
| 2002/0070970 A1 | 6/2002 | Wood et al. |
| 2002/0075997 A1 | 6/2002 | Unger et al. |
| 2002/0090055 A1 | 7/2002 | Zur et al. |
| 2002/0094062 A1 | 7/2002 | Dolazza |
| 2002/0122533 A1 | 9/2002 | Marie et al. |
| 2002/0126798 A1 | 9/2002 | Harris |
| 2003/0007598 A1 | 1/2003 | Wang et al. |
| 2003/0010923 A1 | 1/2003 | Zur |
| 2003/0018272 A1 | 1/2003 | Treado et al. |
| 2003/0026386 A1 | 2/2003 | Tang et al. |
| 2003/0058989 A1 | 3/2003 | Rotondo |
| 2003/0072409 A1 | 4/2003 | Kaufhold et al. |
| 2003/0072417 A1 | 4/2003 | Kaufhold et al. |
| 2003/0073895 A1 | 4/2003 | Nields et al. |
| 2003/0095624 A1 | 5/2003 | Eberhard et al. |
| 2003/0097055 A1 | 5/2003 | Yanof et al. |
| 2003/0149364 A1 | 8/2003 | Kapur |
| 2003/0169847 A1 | 9/2003 | Karellas et al. |
| 2003/0194050 A1 | 10/2003 | Eberhard |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0212327 A1 | 11/2003 | Wang et al. |
| 2003/0215120 A1 | 11/2003 | Uppaluri et al. |
| 2004/0008809 A1 | 1/2004 | Webber |
| 2004/0066882 A1 | 4/2004 | Eberhard et al. |
| 2004/0066884 A1 | 4/2004 | Hermann Claus |
| 2004/0066904 A1 | 4/2004 | Eberhard et al. |
| 2004/0070582 A1 | 4/2004 | Smith et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0146221 A1 | 7/2004 | Siegel et al. |
| 2004/0170561 A1* | 9/2004 | Saib ................ A61B 6/4035 424/9.4 |
| 2004/0171986 A1 | 9/2004 | Tremaglio, Jr. et al. |
| 2004/0190682 A1 | 9/2004 | Deuringer |
| 2004/0213378 A1 | 10/2004 | Zhou et al. |
| 2004/0247081 A1 | 12/2004 | Halsmer |
| 2004/0264627 A1 | 12/2004 | Besson |
| 2004/0267157 A1 | 12/2004 | Miller et al. |
| 2005/0025278 A1 | 2/2005 | Hagiwara |
| 2005/0049521 A1 | 3/2005 | Miller et al. |
| 2005/0063509 A1 | 3/2005 | DeFreitas et al. |
| 2005/0078797 A1 | 4/2005 | Danielsson et al. |
| 2005/0089205 A1 | 4/2005 | Kapur |
| 2005/0105679 A1 | 5/2005 | Wu et al. |
| 2005/0113681 A1 | 5/2005 | DeFreitas et al. |
| 2005/0113715 A1 | 5/2005 | Schwindt et al. |
| 2005/0117694 A1 | 6/2005 | Francke |
| 2005/0129172 A1 | 6/2005 | Mertelmeier |
| 2005/0133706 A1 | 6/2005 | Eberhard |
| 2005/0135555 A1 | 6/2005 | Claus et al. |
| 2005/0135664 A1 | 6/2005 | Kaufhold et al. |
| 2005/0226375 A1 | 10/2005 | Eberhard et al. |
| 2005/0248347 A1 | 11/2005 | Damadian |
| 2006/0030784 A1 | 2/2006 | Miller et al. |
| 2006/0034426 A1 | 2/2006 | Freudenberger |
| 2006/0074288 A1 | 4/2006 | Kelly |
| 2006/0098855 A1 | 5/2006 | Gkanatsios et al. |
| 2006/0109951 A1 | 5/2006 | Popescu |
| 2006/0126780 A1 | 6/2006 | Rotondo |
| 2006/0129062 A1 | 6/2006 | Nicoson et al. |
| 2006/0155209 A1 | 7/2006 | Miller et al. |
| 2006/0210016 A1 | 9/2006 | Francke |
| 2006/0262898 A1 | 11/2006 | Partain |
| 2006/0269041 A1 | 11/2006 | Mertelmeier |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0076844 A1 | 4/2007 | Defreitas et al. |
| 2007/0078335 A1 | 4/2007 | Horn |
| 2007/0140419 A1 | 6/2007 | Souchay |
| 2007/0217573 A1* | 9/2007 | Bernhardt ............ A61B 6/463 378/98.12 |
| 2007/0223651 A1 | 9/2007 | Wagenaar et al. |

(56) References Cited

U.S. PATENT DOCUMENTS

| | | |
|---|---|---|
| 2007/0225600 A1 | 9/2007 | Weibrecht et al. |
| 2007/0242800 A1 | 10/2007 | Jing et al. |
| 2007/0280412 A1 | 12/2007 | DeFreitas |
| 2008/0019581 A1 | 1/2008 | Gkanatsios et al. |
| 2008/0045833 A1 | 2/2008 | Defreitas et al. |
| 2008/0056436 A1 | 3/2008 | Pack |
| 2008/0101537 A1 | 5/2008 | Sendai |
| 2008/0112534 A1 | 5/2008 | Defreitas |
| 2008/0118023 A1 | 5/2008 | Besson |
| 2008/0130979 A1 | 6/2008 | Ren |
| 2008/0212861 A1 | 9/2008 | Durgan et al. |
| 2008/0285712 A1 | 11/2008 | Kopans |
| 2008/0317196 A1 | 12/2008 | Imai |
| 2009/0003519 A1 | 1/2009 | Defreitas et al. |
| 2009/0010384 A1 | 1/2009 | Jing et al. |
| 2009/0080594 A1 | 3/2009 | Brooks et al. |
| 2009/0080602 A1 | 3/2009 | Brooks et al. |
| 2009/0135997 A1 | 5/2009 | Defreitas et al. |
| 2009/0141859 A1 | 6/2009 | Gkanatsios et al. |
| 2009/0175408 A1 | 7/2009 | Goodsitt et al. |
| 2009/0213987 A1 | 8/2009 | Stein et al. |
| 2009/0237924 A1 | 9/2009 | Ladewig |
| 2009/0238424 A1 | 9/2009 | Arakita et al. |
| 2009/0262887 A1 | 10/2009 | Iordache |
| 2009/0268865 A1 | 10/2009 | Ren et al. |
| 2009/0296882 A1 | 12/2009 | Gkanatsios |
| 2009/0304147 A1 | 12/2009 | Jing et al. |
| 2010/0020937 A1 | 1/2010 | Hautmann |
| 2010/0020938 A1 | 1/2010 | Koch |
| 2010/0034450 A1 | 2/2010 | Mertelmeier |
| 2010/0054400 A1 | 3/2010 | Ren |
| 2010/0086188 A1 | 4/2010 | Ruth |
| 2010/0091940 A1 | 4/2010 | Ludwig et al. |
| 2010/0150306 A1 | 6/2010 | Defreitas et al. |
| 2010/0189227 A1 | 7/2010 | Mannar |
| 2010/0195882 A1 | 8/2010 | Ren |
| 2010/0226475 A1 | 9/2010 | Smith |
| 2010/0290585 A1 | 11/2010 | Eliasson |
| 2010/0303202 A1 | 12/2010 | Ren |
| 2010/0313196 A1 | 12/2010 | De Atley |
| 2011/0026667 A1 | 2/2011 | Poorter |
| 2011/0069809 A1 | 3/2011 | Defreitas et al. |
| 2011/0178389 A1 | 7/2011 | Kumar et al. |
| 2011/0188624 A1 | 8/2011 | Ren |
| 2011/0234630 A1 | 9/2011 | Batman et al. |
| 2011/0257919 A1 | 10/2011 | Reiner |
| 2011/0268246 A1 | 11/2011 | Dafni |
| 2012/0033868 A1 | 2/2012 | Ren |
| 2012/0051502 A1 | 3/2012 | Ohta et al. |
| 2012/0236987 A1 | 9/2012 | Ruimi |
| 2012/0238870 A1* | 9/2012 | Smith .......... A61B 6/466 600/431 |
| 2013/0028374 A1 | 1/2013 | Gkanatsios et al. |
| 2013/0211261 A1 | 8/2013 | Wang |
| 2013/0272493 A1 | 10/2013 | Otokuni |
| 2013/0272494 A1 | 10/2013 | DeFreitas et al. |
| 2014/0044230 A1 | 2/2014 | Stein et al. |
| 2014/0044231 A1 | 2/2014 | Defreitas et al. |
| 2014/0086471 A1 | 3/2014 | Ruth et al. |
| 2014/0098935 A1 | 4/2014 | Defreitas et al. |
| 2014/0232752 A1 | 8/2014 | Ren et al. |
| 2014/0314198 A1 | 10/2014 | Ren et al. |
| 2014/0321607 A1 | 10/2014 | Smith |
| 2014/0328458 A1 | 11/2014 | Erhard |
| 2014/0376690 A1 | 12/2014 | Jing et al. |
| 2015/0049859 A1 | 2/2015 | DeFreitas et al. |
| 2015/0160848 A1 | 6/2015 | Gkanatsios et al. |
| 2015/0310611 A1 | 10/2015 | Gkanatsios et al. |
| 2016/0066875 A1 | 3/2016 | Jacob et al. |
| 2016/0106383 A1 | 4/2016 | Ren et al. |
| 2016/0189376 A1 | 6/2016 | Bernard |
| 2016/0209995 A1 | 7/2016 | Jeon |
| 2016/0220207 A1 | 8/2016 | Jouhikainen |
| 2016/0256125 A1 | 9/2016 | Smith |
| 2016/0270742 A9 | 9/2016 | Stein et al. |
| 2016/0302746 A1 | 10/2016 | Erhard |
| 2016/0331339 A1 | 11/2016 | Guo |
| 2017/0024113 A1 | 1/2017 | Gkanatsios et al. |
| 2017/0032546 A1 | 2/2017 | Westerhoff |
| 2017/0071562 A1 | 3/2017 | Suzuki |
| 2017/0128028 A1 | 5/2017 | DeFreitas et al. |
| 2017/0135650 A1 | 5/2017 | Stein et al. |
| 2017/0316588 A1 | 11/2017 | Homann |
| 2017/0319167 A1 | 11/2017 | Goto |
| 2017/0367674 A1 | 12/2017 | Arai et al. |
| 2018/0130201 A1 | 5/2018 | Bernard |
| 2018/0177476 A1 | 6/2018 | Jing et al. |
| 2018/0188937 A1 | 7/2018 | Gkanatsios et al. |
| 2018/0289347 A1 | 10/2018 | DeFreitas et al. |
| 2018/0344276 A1 | 12/2018 | DeFreitas et al. |
| 2019/0059830 A1 | 2/2019 | Williams |
| 2019/0095087 A1 | 3/2019 | Gkanatsios et al. |
| 2019/0200942 A1 | 7/2019 | DeFreitas |
| 2019/0336794 A1 | 11/2019 | Li |
| 2019/0388051 A1 | 12/2019 | Morita |
| 2020/0012417 A1 | 1/2020 | Gkanatsios |
| 2020/0029927 A1 | 1/2020 | Wilson |
| 2020/0085393 A1 | 3/2020 | Zhang |
| 2020/0222023 A1 | 7/2020 | Wong |
| 2020/0348835 A1 | 11/2020 | Gkanatsios |
| 2020/0352531 A1 | 11/2020 | Smith |
| 2021/0128087 A1 | 5/2021 | DeFreitas |
| 2022/0071582 A1 | 3/2022 | DeFreitas |
| 2022/0378389 A1 | 12/2022 | Wong |
| 2023/0000455 A1 | 1/2023 | Wong |

FOREIGN PATENT DOCUMENTS

| | | |
|---|---|---|
| DE | 102004051401 | 5/2006 |
| DE | 102004051820 | 5/2006 |
| DE | 102010027871 | 10/2011 |
| EP | 0775467 | 5/1997 |
| EP | 0982001 | 3/2000 |
| EP | 1028451 | 8/2000 |
| EP | 1428473 | 6/2004 |
| EP | 1759637 | 3/2007 |
| EP | 1569556 | 4/2012 |
| EP | 2732764 | 5/2014 |
| EP | 2602743 | 11/2014 |
| EP | 2819145 | 12/2014 |
| EP | 3143935 | 3/2017 |
| JP | 53151381 U | 11/1978 |
| JP | 2001-346786 | 12/2001 |
| JP | 2002219124 | 8/2002 |
| JP | 2006-231054 | 9/2006 |
| JP | 2007-50264 | 3/2007 |
| JP | 2007-521911 | 8/2007 |
| JP | 2007229269 | 9/2007 |
| JP | 2008-67933 | 3/2008 |
| JP | 2008086471 | 4/2008 |
| JP | 2009500048 | 1/2009 |
| JP | 2011-072667 | 4/2011 |
| JP | 2011-250842 | 12/2011 |
| JP | 2012-509714 | 4/2012 |
| JP | 2012-511988 | 5/2012 |
| JP | 2015-530706 | 10/2015 |
| WO | WO 90/05485 | 5/1990 |
| WO | WO 9803115 | 1/1998 |
| WO | WO 98/16903 | 4/1998 |
| WO | WO 00/51484 | 9/2000 |
| WO | WO 03/020114 | 3/2003 |
| WO | WO 03037046 | 5/2003 |
| WO | WO 2003/057564 | 7/2003 |
| WO | WO 2004/043535 | 5/2004 |
| WO | WO 2005/051197 | 6/2005 |
| WO | WO 2005/110230 | 11/2005 |
| WO | WO 2005/112767 | 12/2005 |
| WO | WO 2006/055830 | 5/2006 |
| WO | WO 2006/058160 | 6/2006 |
| WO | WO 2007129244 | 11/2007 |
| WO | WO 2008072144 | 6/2008 |
| WO | WO 2009122328 | 10/2009 |
| WO | WO 2009136349 | 11/2009 |
| WO | WO 2010/070554 | 6/2010 |

(56) References Cited

FOREIGN PATENT DOCUMENTS

| WO | WO 2011/058730 | 5/2011 |
|---|---|---|
| WO | WO 2013/184213 | 12/2013 |
| WO | WO 2014/176445 | 10/2014 |
| WO | WO 2018/170265 | 9/2018 |

OTHER PUBLICATIONS

"Filtered Back Projection," (NYGREN) published May 8, 2007; URL:http://web.archive.org/web/19991010131715/http://www.owlnet.rice.edu/-.about.elec539/Projects97/cult/node2.html., 2 pgs.

"Lorad Selenia" Document B-BI-SEO US/Intl (May 2006) copyright Hologic 2006, 12 pgs.

Acrin website, located at https://www.acrin.org/PATIENTS/ABOUTIMAGINGEXAMSANDAGENTS/ABOUTMAMMOGRAPHYANDTOMOSYNTHESIS.aspx, "About Mammography and Tomosynthesis", obtained online on Dec. 8, 2015, 5 pgs.

American College of Radiology website, located at http://www.acr.org/FAQs/DBT-FAQ, "Digital Breast Tomosynthesis FAQ For Insurers", obtained online on Dec. 8, 2015, 2 pages.

Aslund, Magnus, "Digital Mammography with a Photon Counting Detector in a Scanned Multislit Geometry", Doctoral Thesis, Dept of Physics, Royal Institute of Technology, Stockholm, Sweden, Apr. 2007, 51 pages.

Chan, Heang-Ping et al., "ROC study of the effect of stereoscopic imaging on assessment of breast lesions", Medical Physics, vol. 32, No. 4, Apr. 2005, 7 pgs.

Cole, Elodia, et al., "The Effects of Gray Scale Image Processing on Digital Mammography Interpretation Performance", Academic Radiology, vol. 12, No. 5, pp. 585-595, May 2005.

Digital Clinical Reports, Tomosynthesis, GE Brochure 98-5493, Nov. 1998, 8 pgs.

Dobbins, James T., "Digital x-ray tomosynthesis: current state of the art and clinical potential," Physics in Medicine and Biology, Taylor and Francis LTD, London GB, vol. 48, No. 19, Oct. 7, 2003, 42 pages.

Grant, David G., "Tomosynthesis: a three-dimensional imaging technique", IEEE Trans. Biomed. Engineering, vol. BME-19, #1, Jan. 1972, pp. 20-28.

Japanese Notice of Rejection in Application 2018-554775, dated Feb. 22, 2021, 10 pages.

Japanese Office Action mailed in Application 2016-087710, dated Mar. 1, 2017, 5 pages.

Japanese Office Action mailed in Application 2017-001579, dated Mar. 29, 2017, 1 page. (No English Translation.).

Kachelriess, Marc et al., "Flying Focal Spot (FFS) in Cone-Beam CT", 2004 IEEE Nuclear Science Symposium Conference Record, Oct. 16-22, 2004, Rome Italy, vol. 6, pp. 3759-3763.

Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.

Mammographic Accreditation Phantom, http://www.cirsinc.com/pdfs/015cp.pdf. (2006), 2 pgs.

Niklason et al., "Digital breast tomosynthesis: potentially a new method for breast cancer screening", In Digital Mammography, 1998, 6 pages.

Niklason, Loren T. et al., "Digital Tomosynthesis in Breast Imaging", Radiology, Nov. 1997, vol. 205, No. 2, pp. 399-406.

Pediconi, Federica et al., "Color-coded automated signal intensity-curve for detection and characterization of breast lesions: Preliminary evaluation of a new software for MR-based breast imaging", International Congress Series 1281 (2005) 1081-1086.

Pisano, Etta D., "Digital Mammography", Radiology, vol. 234, No. 2, Feb. 2005, pp. 353-362.

Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.

Smith, A., "Fundamentals of Breast Tomosynthesis", White Paper, Hologic Inc., WP-00007, Jun. 2008, 8 pgs.

Smith, Andrew, PhD, "Full Field Breast Tomosynthesis", Hologic White Paper, Oct. 2004, 6 pgs.

Thurfjell, "Mammography screening: one versus two views and independent double reading", Acta Radiologica 35, No. 4, 1994, pp. 345-350.

Wheeler F. W., et al. "Micro-Calcification Detection in Digital Tomosynthesis Mammography", Proceedings of SPIE, Conf-Physics of Semiconductor Devices, Dec. 11, 2001 to Dec. 15, 2001, Delhi, SPIE, US, vol. 6144, Feb. 13, 2006, 12 pgs.

Wu, Tao, et al. "Tomographic Mammography Using a Limited Number of Low-Dose Cone-Beam Projection Images" Medical Physics, AIP, Melville, NY, vol. 30, No. 3, Mar. 1, 2003, p. 365-380.

* cited by examiner

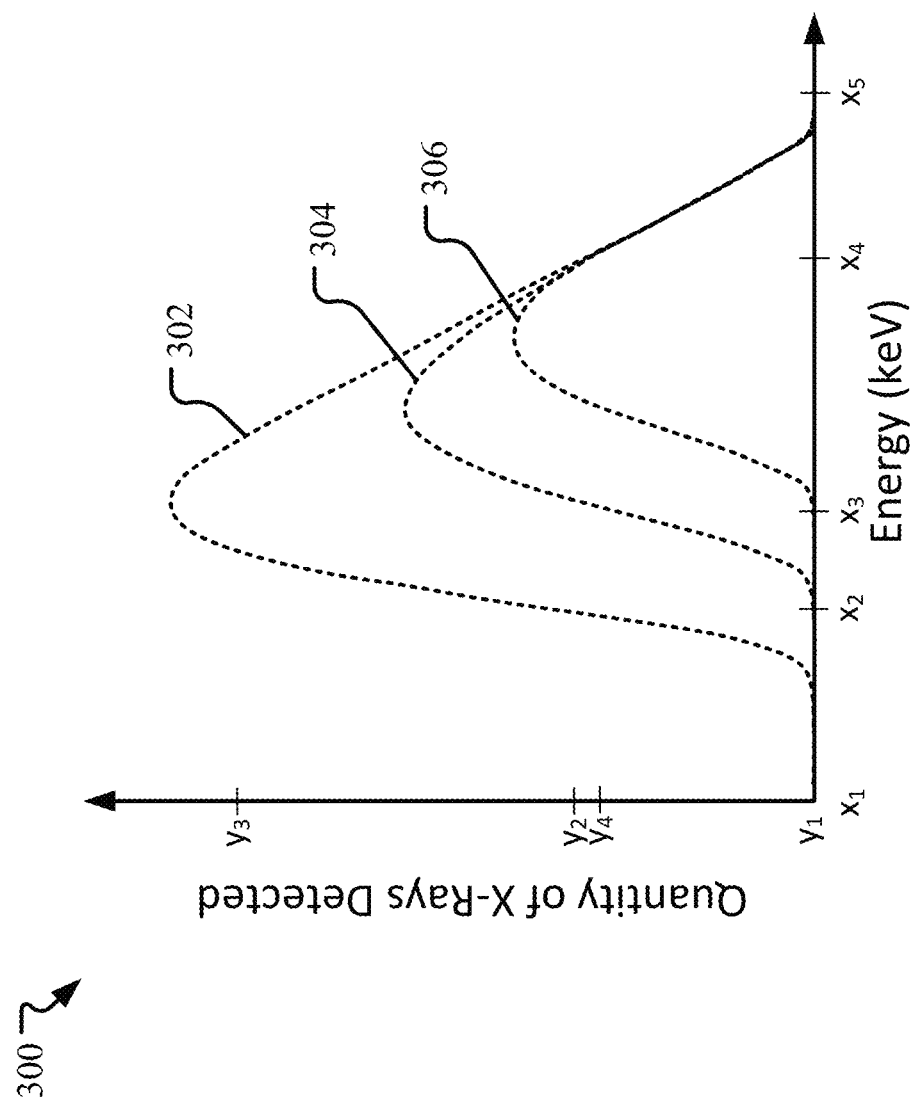

CONTRAST-ENHANCED TOMOSYNTHESIS WITH A COPPER FILTER

INTRODUCTION

Medical imaging is used for detection of cancerous cells in breast tissue. A plurality of different imaging processes, image acquisition parameters, and image processing techniques are used to enhance images for better detection of abnormal tissue.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods relating to contrast-enhanced tomosynthesis with a copper filter. In an aspect, the technology relates to a method for contrast-enhanced tomosynthesis imaging. The method includes compressing a breast of a patient, the patient's breast positioned substantially between an x-ray source and an x-ray detector, wherein a filter is positioned between the x-ray source and the patient's breast, and wherein the patient's breast has been exposed to a contrast agent. Additionally, the method includes acquiring, while compressing the patient's breast, a plurality of tomosynthesis projection images at an x-ray dose passing through the filter, wherein the filter proportionally filters a subset of energies of the x-ray dose, wherein the x-ray dose includes at least one x-ray energy greater than 40 keV. Further, the method includes processing the plurality of tomosynthesis projection images to obtain a plurality of filtered reconstructed tomosynthesis slice images; and displaying at least one image of the filtered reconstructed tomosynthesis slice images.

In an example, the filter includes copper. In another example, the subset of energies of the x-ray dose proportionally filtered by the filter includes at least one energy below 30 keV. In a further example, the subset of energies of the x-ray dose proportionally filtered by the filter includes energies below 40 keV. In yet another example, the contrast agent has an absorption of the x-ray dose that is greater for higher energies.

In another aspect, an apparatus for contrast-enhanced tomosynthesis imaging is disclosed. The apparatus includes: an x-ray source capable of selectively moving relative to a patient's breast; an imaging x-ray detector; a compression mechanism for compressing the patient's breast, the compression mechanism disposed between the x-ray source and the imaging x-ray detector; a filter insertable into the apparatus between the x-ray source and the patient's breast, wherein the filter proportionally filters a subset of energies of an x-ray dose emittable by the x-ray source; a processor; and memory storing instructions that, when executed by the processor, cause the apparatus to perform a set of operations. The set of operations includes selectively moving the x-ray source through at a plurality of selectable positions while emitting an x-ray dose from the x-ray source. Additionally, the set of operations includes detecting, by the x-ray detector, the x-ray dose from the plurality of selectable positions, after the x-ray dose passes through the filter and the patient's breast. Based on the detected x-ray dose from the plurality of selectable positions, the set of operations includes generating, by the processor operatively connected to the x-ray detector, a plurality of tomosynthesis projection images. The set of operations further includes processing, by the processor, the plurality of tomosynthesis projection images to obtain a plurality of filtered reconstructed tomosynthesis slice images.

In an example, the filter of the apparatus includes an element with an atomic number of at least 21. In another example, the filter comprises as sheet member that has a thickness ranging from 0.1 mm to 0.5 mm. In a further example, the sheet member of the filter comprises copper. In yet another example, the apparatus further includes a tilting mechanism to tilt the patient's breast as the x-ray source selectively moves through the plurality of selectable positions.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

The accompanying figures illustrate one or more aspects of the disclosed methods and systems. In the appended figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label. Non-limiting and non-exhaustive examples are described with reference to the following figures:

FIG. 3 depicts a graph of a quantity of x-rays detected versus energy.

Figure 1A:
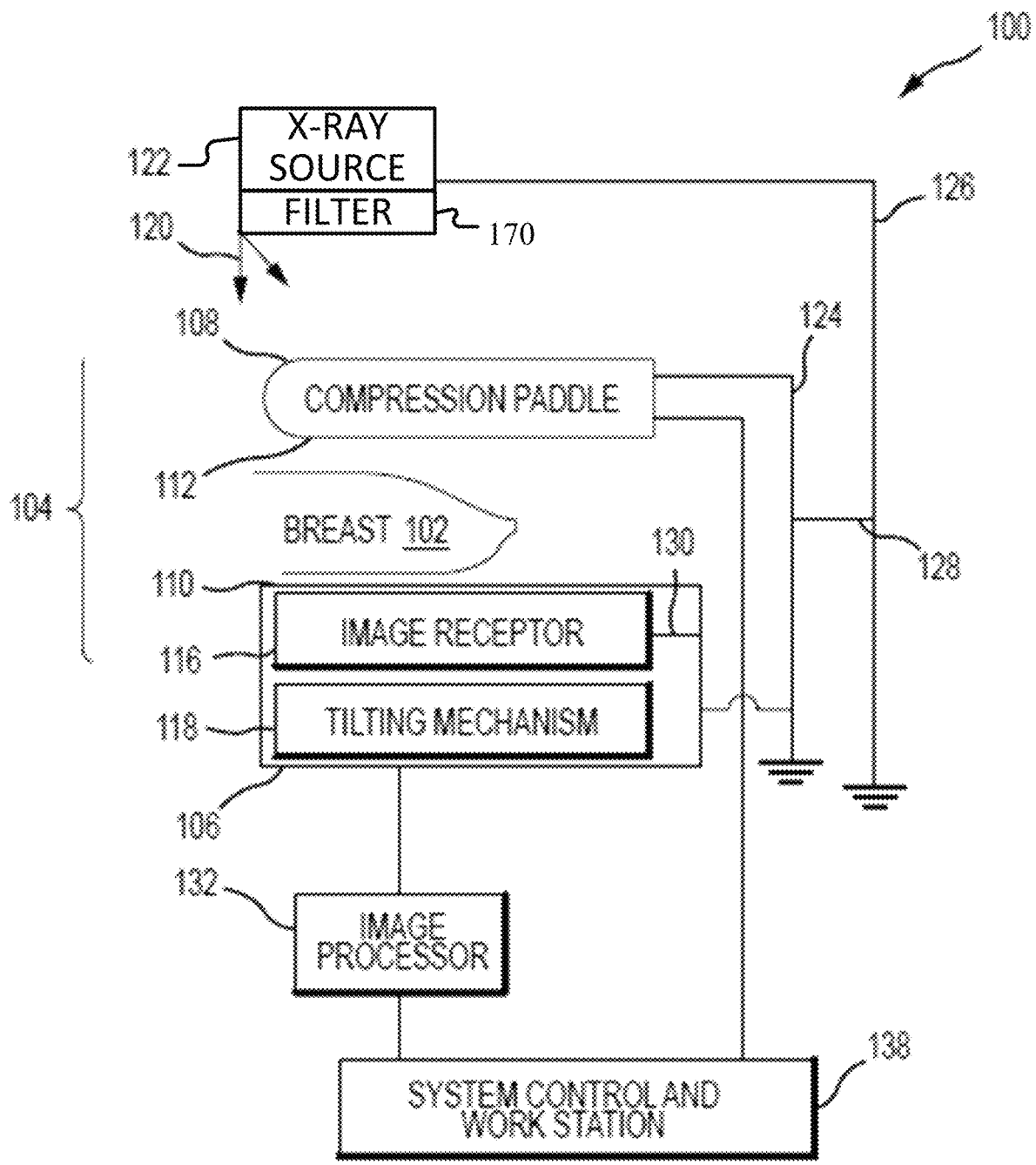
FIG. 1A depicts is a schematic view of an exemplary imaging system.

While examples of the disclosure are amenable to various modifications and alternate forms, specific examples have been shown by way of example in the drawings and are described in detail below. The intention is not to limit the scope of the disclosure to the particular examples described. On the contrary, the disclosure is intended to cover all modifications, equivalents, and alternatives falling within the scope of the disclosure and the appended claims.

DETAILED DESCRIPTION

Various aspects of the disclosure are described more fully below, with reference to the accompanying drawings, which show specific example aspects. However, different aspects of the disclosure may be implemented in many different forms and should not be construed as limited to the aspects described herein; rather, these aspects are provided so that this disclosure will be thorough and complete and will fully convey the scope of the aspects to those skilled in the art. Aspects may be practiced as methods, systems, or devices. The following detailed description is, therefore, not to be interpreted in a limiting sense.

Breast cancer is one of the leading causes of cancer-related mortality of women. A mammogram is an x-ray image of inner breast tissue that is used to visualize normal and abnormal structures within a breast. Mammography is commonly used for breast cancer screening, diagnosis, and evaluation, because mammography often shows breast lumps and/or calcifications before they are manually palpable, thus providing early tumor detection.

Mammography presents difficulties, however, when determining whether a detected abnormality is cancerous or benign. This may be due to mammography resulting in a two-dimensional projection image representing a three-dimensional structure of the breast. Overlapping structures in the compressed breast may confound image interpretation and diagnosis of a two-dimensional image. Mammography may also present difficulty in determining cancerous or benign cells because the x-rays that are often used to obtain the mammography image have energies that are in a range that helps achieve a desirable Signal to Noise Ratio (SNR) but at the same time may cause the x-rays to be attenuated to a similar degree by breast structures that may have different clinical significance.

Efforts to improve the sensitivity and specificity of breast x-rays have included the development of breast tomosynthesis systems. Breast tomosynthesis is a three-dimensional imaging technology that involves acquiring images of a stationary compressed breast at multiple angles during a short scan (otherwise referred to herein as a sweep). The individual projection tomosynthesis images taken at respective angles of the imaging x-ray beam relative to the breast are then computer-processed into a series of reconstructed tomosynthesis slice images, each representing a respective slice of the breast. The tomosynthesis projection images or reconstructed slice images can be displayed individually, concurrently, or dynamically.

Breast tomosynthesis typically uses a field digital mammography (FFDM) platform. In one example, an x-ray tube moves in an arc above the breast and a series of 11 to 22 low dose x-ray 2-D tomosynthesis projection images are obtained (i.e., a tomosynthesis scan or a tomosynthesis sweep). The sum of the dose from all of the 2-D tomosynthesis projection images may be similar to the dose from a single conventional digital mammogram. These low-dose 2-D tomosynthesis projection images are reconstructed into a series of 3-D slice images, each representing a slice of the breast where each slice is, for example, 1-5 mm thick. The slice images typically conform to planes parallel to the platform supporting the breast during image acquisition, but could be oriented differently. An advantage of breast tomosynthesis compared to conventional mammography is that, by showing the breast as a series of slices rather than a single mammogram, a lesion may be seen with greater clarity because much of the superimposed tissue present in a conventional mammogram has been removed.

Reconstructed tomosynthesis slice images reduce or eliminate problems caused by tissue overlap and structure noise in two-dimensional mammography imaging. Digital breast tomosynthesis also offers the possibility of reduced breast compression, improved diagnostic and screening accuracy, fewer recalls, and 3D lesion localization. An example of a multi-mode breast tomosynthesis/mammography system is described in commonly assigned U.S. Pat. No. 7,869,563. Other aspects of breast tomosynthesis and mammography are described in commonly assigned U.S. Pat. Nos. 7,991,106, 7,760,924, 7,702,142, 7,245,694, and 9,020,579, which are hereby incorporated by reference.

In an effort to improve imaging to differentiate cancerous tissue from benign abnormalities in breast x-ray imaging, consideration has been given to contrast-enhanced imaging and dual-energy imaging. In contrast-enhanced imaging, a contrast agent is introduced into the breast, typically through an injection in a vein remote from the breast, and x-ray images are taken after (as well as possibly before) the contrast agent has reached the breast. In an example, a contrast agent is iodine-based. The contrast agent may illuminate with high-energy x-rays, which may depend on the atomic number of the contrast agent. The contrast agent helps highlight vascularity in the breast. If images of the same breast taken before and after the arrival of the contrast agent in the breast are subtracted from each other (and absent breast motion between the times the two images are taken), breast vascularity may appear more clearly in the resulting subtraction image. Imaging of the vessels around a tumor is believed to allow improved detection of breast cancer. The use of contrast agents may be used in a variety of x-ray imaging methods, including breast CT, breast tomosynthesis, and digital mammography.

In x-ray breast mammography or tomosynthesis, contrast enhanced images are obtained using two methods. The first involves subtraction of images obtained pre-contrast agent and post-contrast agent. This method is referred to as time subtraction. The second method is referred to as dual-energy contrast imaging. In this method images are obtained at low energy and high energy after the injection of a contrast agent. The images are obtained at energies above and below a K-absorption edge (k-edge) of the contrast agent (e.g., for iodine, 33.2 keV). At x-ray energies just above the k-edge, the absorption of x-rays is increased, resulting in an increase of contrast from the iodine contrast agent in the high energy image. Subtraction of these two images enhances iodine contrast while suppressing the contrast of normal breast anatomy. An advantage of dual-energy contrast enhanced mammography is that both images may be obtained in a very short time and therefore the images may be subtracted with little patient motion. This is not true for subtraction of pre-contrast agent and post-contrast agent images because typically there will be more than a minute separating the acquisition of the two images.

For contrast-enhanced methods using subtraction (e.g., time subtraction or dual-energy subtraction), the imaging equipment uses software-based techniques. Additionally, for dual-energy imaging, software is needed to control the energy of x-rays emitted (e.g., high energy or low energy). Not all imaging devices are equipped with processing power or software that is capable of subtraction techniques or controlling energy of x-rays. For imaging devices that may not have these software or processing capabilities, or for imaging devices for which integrate these capabilities would be too costly, other improvements of breast tomosynthesis may be considered.

Accordingly, the present disclosure provides systems and methods for enhancing images acquired using breast tomosynthesis, without image subtraction or dual-energy imaging. The present technology provides performing breast tomosynthesis in the presence of an x-ray filter. For example, an x-ray filter may be placed between an x-ray source and breast tissue. The filter may proportionally filter out a subset of the energies emitted by the x-ray source. A filter may include characteristics to filter x-ray energies based on a k-edge of a contrast agent introduced into the breast, such that the breast tissue has relatively greater exposure to x-ray energies above the k-edge of the contrast agent to illuminate the contrast agent without substantial illumination of other breast tissue. Thus, tomosynthesis images similar to those obtained using subtraction may be acquired without software-based contrast enhancing techniques.

Figure 1B:
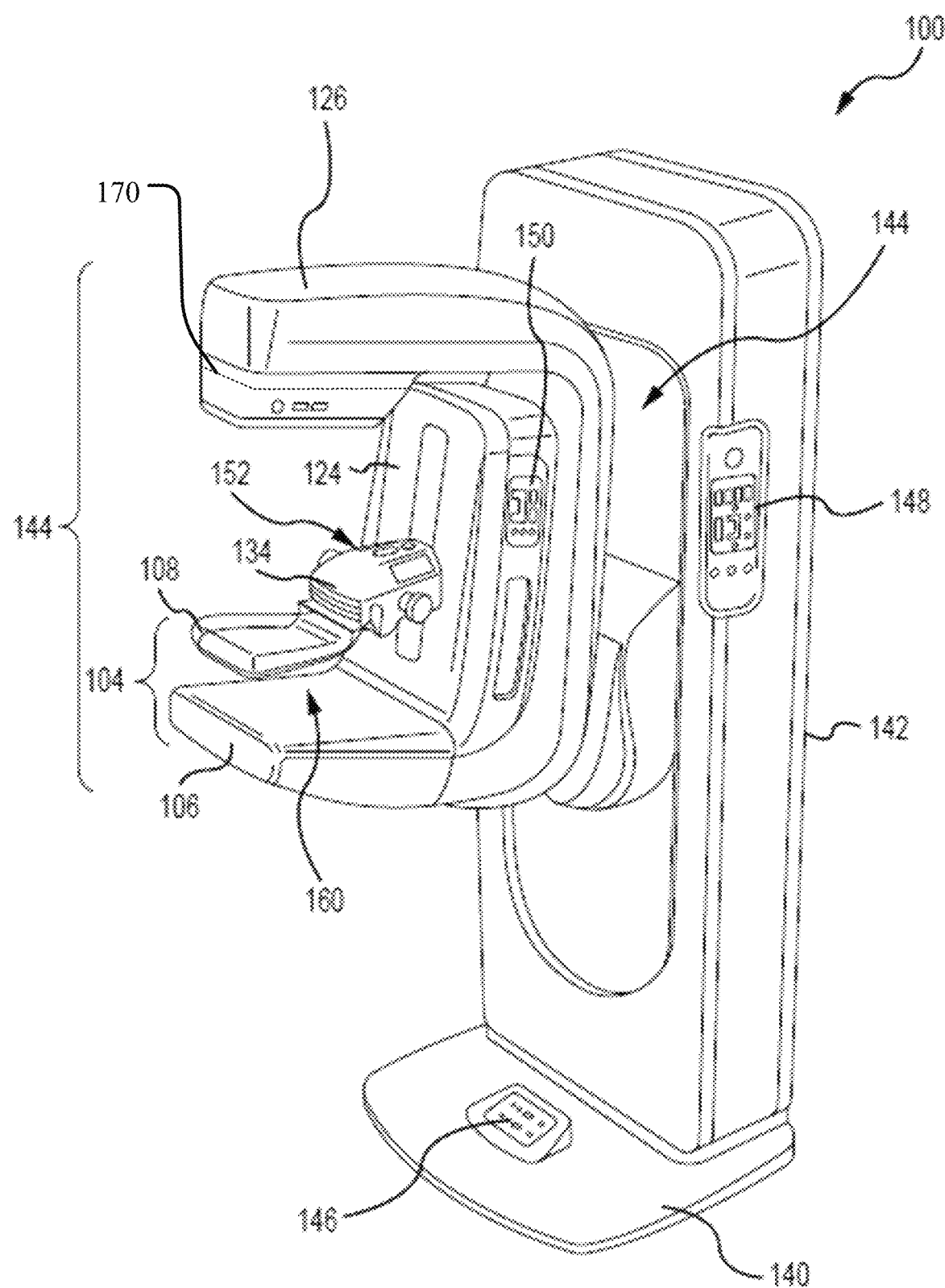
FIG. 1B depicts a perspective view of the imaging system of FIG. 1A

FIGS. 1A-1B show different views of an example imaging system 100. Specifically, FIG. 1A is a schematic view of the example imaging system 100. FIG. 1B is a perspective view of the imaging system 100. Referring concurrently to FIGS. 1A and 1B, not every element described below is depicted in both figures. The imaging system 100 immobilizes a patient's breast 102 for x-ray imaging (either or both of mammography and tomosynthesis) via a breast compression immobilizer unit 104 that includes a static breast support platform 106 and a foam compressive element 108. Different paddles, each having different purposes, are known in the art. Certain examples paddles are also described herein for context. The breast support platform 106 and the foam compressive element 108 each have a compression surface 110 and 112, respectively, that move towards each other to compress, immobilize, stabilize, or otherwise hold and secure the breast 102 during imaging procedures. In known systems, the compression surface 110, 112 is exposed so as to directly contact the breast 102. Compression surface 110 may be a rigid plastic, a flexible plastic, a resilient foam, a mesh or screen, and so on. Compression surface 112 is a lower surface of the foam compressive element 108. The platform 106 also houses an image receptor 116 and, optionally, a tilting mechanism 118, and optionally an anti-scatter grid (not depicted, but disposed above the image receptor 116). The immobilizer unit 104 is in a path of an imaging beam 120 emanating from x-ray source 122, such that the beam 120 impinges on the image receptor 116.

The immobilizer unit 104 is supported on a first support arm 124 via a compression arm 134, which is configured to be raised and lowered along the support arm 124. The x-ray source 122 is supported on a second support arm, also referred to as a tube head 126. For mammography, support arms 124 and 126 can rotate as a unit about an axis 128 between different imaging orientations such as craniocaudal (CC) and mediolateral oblique (MLO), so that the system 100 can take a mammogram projection image at each orientation. (The terms front, lower, and upper pertain to using a CC imaging orientation, with the patient facing the front of the imaging system, although it should be understood that other imaging orientations, including MLO, are used with the same equipment.) In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102.

Concurrently and optionally, the image receptor 116 may be tilted relative to the breast support platform 106 and in sync with the rotation of the second support arm 126. The tilting can be through the same angle as the rotation of the x-ray source 122 but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging. An example of such a combo system has been offered by the assignee hereof under the trade name Selenia Dimensions.

When the system is operated, the image receptor 116 produces imaging information in response to illumination by the imaging beam 120 and supplies it to an image processor 132 for processing and generating breast x-ray images. A system control and workstation unit 138 including software controls the operation of the system and interacts with the operator to receive commands and deliver information including processed-ray images.

The imaging system 100 includes a floor mount or base 140 for supporting the imaging system 100 on a floor. A gantry 142 extends upwards from the base 140 and rotatably supports both the tube head 208 and a support arm 210. The tube head 126 and support arm 124 are configured to rotate discretely from each other and may also be raised and lowered along a face 144 of the gantry 142 so as to accommodate patients of different heights. The x-ray source 122 is disposed within the tube head 208. Together, the tube head 126 and support arm 124 may be referred to as a C-arm 124.

A number of interfaces and display screens are disposed on the imaging system 100. These include a foot display screen 146, a gantry interface 148, a support arm interface 150, and a compression arm interface 152. In general, the various interfaces 148, 150, and 152 may include one or more tactile buttons, knobs, switches, as well as one or more display screens, including capacitive touch screens with graphic user interfaces (GUIs) so as to enable user interaction with and control of the imaging system 100. In general, the foot display screen 146 is primarily a display screen, though a capacitive touch screen might be utilized if required or desired.

One challenge with the imaging system 100 is that images may lack sufficient contrast for a radiologist to determine if tissue is cancerous or benign. To improve identification of tissue, an x-ray filter 170 may be used. A filter 170 may filter out x-rays travelling through the filter that are below a certain energy. In an example, lower energies may be filtered out proportionally more than higher energies, up to a threshold energy (above which little to no x-rays are filtered). The filter 170 may be a variety of materials, shapes, sizes, and thickness. Additionally, the filter 170 may be interchangeable or customizable. The filter 170 is positioned in the imaging system 100 to filter out certain x-ray energies of an x-ray beam emitted from an x-ray source 122 prior to the beam passing through the breast 102. For example, the filter 170 may be positioned at the x-ray source 122, such that the x-rays pass through the filter 170 prior to reaching the compression paddle 108 and breast 102. For example, the filter 170 may be positionable on, coupled to, or removably insertable into the tube head 126 or the compression element 108 of the imaging system 100. In another example, the filter may be disposed on the compression paddle (e.g., the filter may be secured to a rigid substrate of the compression paddle.

The effects of the filter 170 may be combined with illumination of a contrast agent. For example, the breast 102 may be introduced to a contrast agent prior to imaging with the imaging system 100. A filter 170 may filter out a subset of energies of an x-ray beam based on the contrast agent (e.g., an appropriate filter 170 may be selected based on a selected contrast agent). The filter 170 may be selectable or interchangeable. For example, an x-ray filter wheel or slide may be provided to switch filters as required or desired. Alternatively, the filter 170 may be manually selected or inserted into the imaging system 100. A variety of different filter materials is appreciated, including rhodium, silver, aluminum, copper, or any other material capable of filtering x-ray energies. By filtering out x-ray energies below the k-edge of the contrast agent, the contrast agent is illuminated with minimal illumination of other aspects of the breast tissue (e.g., which would illuminate at lower x-ray energies).

Figure 2B:
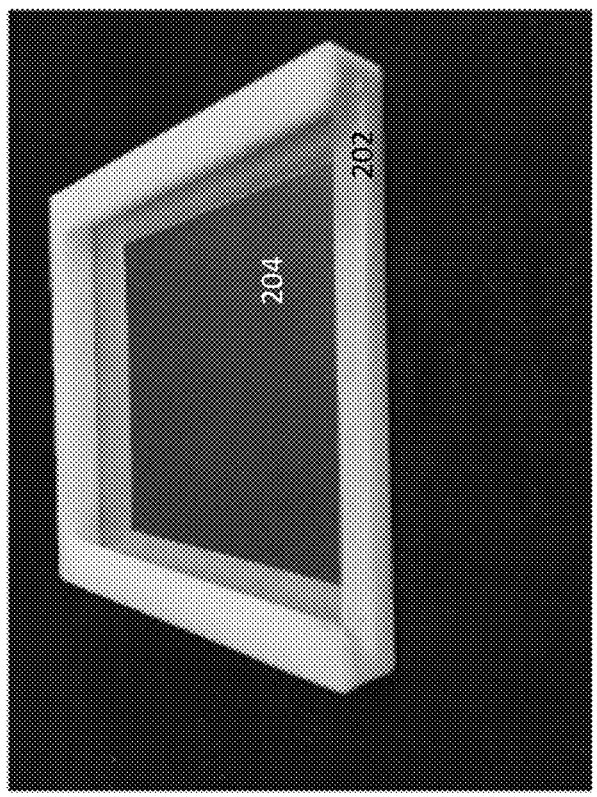
FIG. 2B depicts a bottom perspective view of the example x-ray filter of FIG. 2A.
Figure 2A:
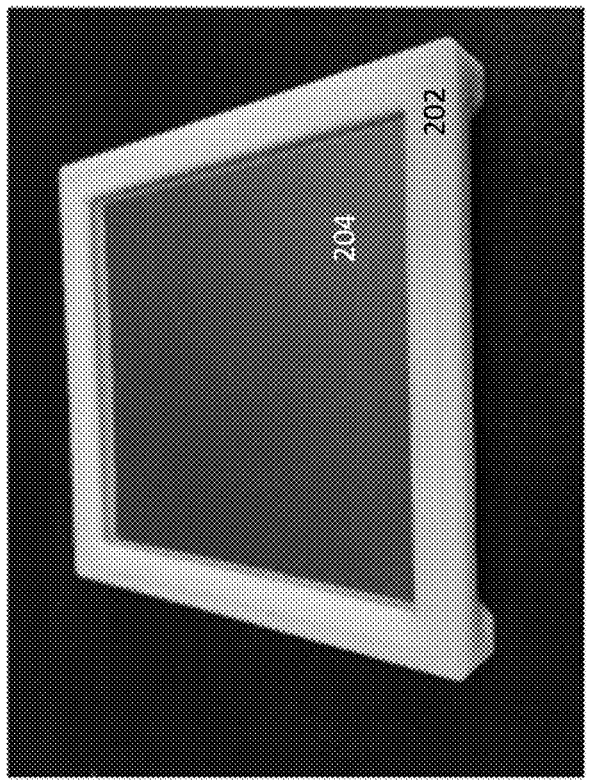
FIG. 2A depicts a top perspective view of an example x-ray filter.

FIGS. 2A-2B depict different views of an example configuration for an x-ray filter 200. Specifically, FIG. 2A shows a top perspective view the x-ray filter 200 and FIG. 2B shows a bottom perspective view of the x-ray filter 200. The filter may include an edge member 202 and a sheet member 204. The edge member 202 is capable of securing a sheet member 204 made of filter material. The edge member 202 may detachably secure the sheet member 204 such that the sheet member 204 may be removed, such as for replacement, cleaning, or repair. For example, the edge member 202 may removably couple to itself about a sheet member 204, frictionally hold the sheet member 204, releasably clamp the sheet member 204, or allow the sheet member 204 to slide in and out, etc. The edge member 202 may accommodate sheet members 204 of a variety of shapes, sizes, thicknesses, and densities. For example, the sheet member may be rectangular, ovular, triangular, etc. Additionally, the edge member 202 may removably couplable to an imaging device (e.g., imaging system 100 in FIGS. 1A-1B). For example, the edge member 202 may be inserted into a slot in the imaging system or attached to an exterior surface of the imaging system (e.g., via hook and loop fasteners, adhesive, clips, screws or an equivalent, etc.).

The sheet member 204, as otherwise described herein, filters out a subset of x-ray energies passing through the sheet member 204. Energies filtered out by the sheet member 204 may be based on a composition of the sheet member 204, including the material and thickness. In an example, the material of the sheet member 204 of the filter 200 includes an element with an atomic number of at least 21. In an instance, the sheet member 204 is composed of copper. Different materials may be associated with filtering of different x-ray energies. Additionally, the thickness of the sheet member 204 may vary. For example, the sheet member 204 may have a thickness between about 0.1 mm and about 1 mm. In another example, the thickness of the sheet member 204 is between about 0.1 mm and about 0.5 mm, such as 0.1 mm, 0.2 mm, 0.3 mm, 0.4 mm, 0.5 mm, or thicknesses approximately the same as those listed. The thickness of the sheet member 204 may be uniform or may vary along the width or length of the sheet member 204. For example, a sheet member 204 with a varying thickness may be adjusted about the imaging device to adjust a quantity of x-rays filtered.

FIG. 3 depicts a graph 300 of a quantity of x-rays detected versus energy. The graph 300 shows an example unfiltered x-ray beam energy profile 302, a first filtered x-ray beam energy profile 304, and a second filtered x-ray beam energy profile 306. In the example shown, the unfiltered x-ray beam energy profile 302 includes energies from energy $x_1$ to energy $x_5$. When applying a first filter (e.g., the quantity of x-rays at the energies of the unfiltered x-ray beam pass through a first sheet member, such as sheet member 204 of filter 200 in FIGS. 2A-2B) to the unfiltered x-ray beam energy profile 302, the first filtered x-ray beam energy profile 304 is obtained. In this example, the first filter (e.g., a sheet member of a filter) is a first thickness and is made of a material that filters energies below energy $x_4$ (i.e., the material of the first filter filters out x-rays below energy $x_4$, which may be at or below a k-edge of a contrast agent). At lower the energies, a greater percentage of x-rays may be filtered out. For example, at energies at or above $x_4$, the unfiltered x-ray beam energy profile 302 is substantially the same as the first filtered x-ray beam energy profile 304 (e.g., at energy $x_4$, both profile 302 and profile 304 have approximately a quantity $y_4$ of x-rays detected). Alternatively, at energies below $x_4$, the quantity of x-rays detected may progressively diverge. In the example shown, the first filtered x-ray beam energy profile 304 includes energies from energy $x_2$, which is greater than $x_1$, to energy $x_5$.

When applying a second filter (e.g., the quantity of x-rays at the energies of the unfiltered x-ray beam pass through a second sheet member, or a different portion of the first sheet member in the case of a varying sheet thickness) to the unfiltered x-ray beam energy profile 302, the second filtered x-ray beam energy profile 306 is obtained. In this example, the second filter is the same material as the first filter (filtering out x-rays below energy $x_4$), but has a thickness greater than the first filter. Similar to the first filter, at lower the energies, a greater percentage of x-rays detected may be filtered out. At a greater thickness, the second filter may filter out more x-rays than the first filter, but still allow x-rays with energies greater than or equal to $x_4$ to pass through. For example, at energies at or above $x_4$, the second filtered x-ray beam energy profile 306 is substantially the same as the unfiltered x-ray beam energy profile 302 and the first filtered x-ray beam energy profile 304 (e.g., at energy $x_4$, profile 302, profile 304, and profile 306 have approximately a quantity $y_4$ of x-rays detected). Alternatively, at energies below $x_4$, the quantity of x-rays detected may progressively diverge from the unfiltered x-ray beam energy profile 302 and the first filtered x-ray beam energy profile 304. In the example shown, the second filtered x-ray beam energy profile 306 includes energies from energy $x_3$, greater than $x_2$, to energy $x_5$.

Thus, filter material may be selected to reduce a quantity of x-rays that have energies below a filtering threshold (e.g., energy $x_4$), which may correspond with a k-edge of a contrast agent (e.g., be at or below the k-edge), and the thickness of the filter may correspond with a relative reduction of the x-rays. In some examples, the filter material may be selected to maximize absorption of x-rays by the contrast agent and/or calcifications in breast tissue. A filter material's impact on its filtering threshold (e.g., energy $x_4$) is based on the filter material's atomic number. In some examples, the filter material may proportionally filter out lower energies than higher energies with a relationship of the third power (e.g., a cubic relationship). As another example, filter material may be selected based on availability or industry-accepted materials. In an instance, a filter may be composed of copper, due in part to regulatory testing of copper filters in the breast imaging industry for 2D imaging.

Figures 4A, 4B:
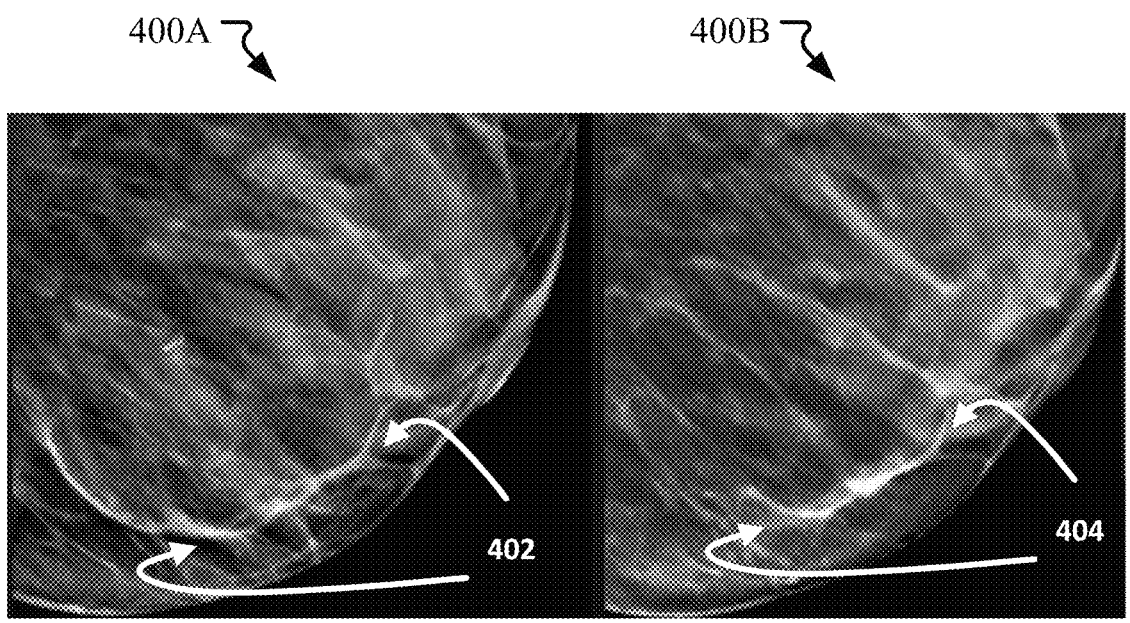
FIG. 4A depicts an example tomosynthesis reconstructed image slice of a breast at a lower x-ray energy.
FIG. 4B depicts an example tomosynthesis reconstructed image slice of the breast of FIG. 4A at a higher x-ray energy as imaged through a filter.

FIGS. 4A-4B show a view of a breast using two different imaging techniques. FIG. 4A depicts an example tomosynthesis reconstructed image slice of a breast at a lower x-ray energy. FIG. 4B depicts an example tomosynthesis reconstructed image slice of the breast of FIG. 4A at a higher x-ray energy as imaged through a filter. In both FIGS. 4A-4B, a contrast agent was introduced into the breast and was present at the time the images were captured.

At lower x-ray energies, contrast in a tomosynthesis image is influenced by soft tissue. At higher x-ray energies, contrast in a tomosynthesis image is influenced by the contrast agent and calcifications. Presence of soft tissue in an x-ray image may interfere with an evaluation of tissue as cancerous or benign. Additionally, it may be advantageous to have better illumination and contrast associated with the presence of a contrast agent and calcification for the tissue evaluation. Thus, imaging of breast tissue may be improved by imaging with higher energy x-rays that are at or above a k-edge of a contrast agent, while filtering out lower energy x-rays to reduce artifacts cause by soft tissue.

By using a filter with a high-energy x-ray beam, high energy x-rays are permitted to travel through the filter and illuminate the contrast agent and calcifications in the breast, while concurrently filtering out lower energy x-rays included in the x-ray beam. The arrangement of a filter with high-energy imaging, while the breast tissue is introduced to a contrast agent, provides an alternative to other contrast-enhanced techniques that may require additional software for x-ray energy control (e.g., for dual-energy imaging) and imaging processing (e.g., for subtraction of two images). The results obtained by using a filter with high-energy x-rays enhance x-ray images of breast tissue (as shown in FIGS. 4A-4B) and produce images that are comparable to images obtained using software-based approaches (as discussed with respect to FIGS. 5A, 5B, 6A, and 6B, below).

As shown in FIG. 4A, which depicts a tomosynthesis reconstructed slice 400A produced from low-energy x-rays without a filter, soft tissue is present in the x-ray image with little differentiation of the illumination of the area of interest 402, which includes a contrast agent and a calcification. Alternatively, in FIG. 4B, which depicts a tomosynthesis reconstructed slice 400B produced from high-energy x-rays with a copper filter, artifacts from soft tissue are reduced while providing greater illumination of the contrast agent and calcification in the area of interest 404. Although FIG. 4B shows a tomosynthesis slice 400B obtained using high-energy x-rays and a filter, any energy x-ray beam should be appreciated. For example, if a filter is used with low-energy x-rays, artifacts from soft tissue will be reduced without significantly reducing illumination of the contrast agent and calcifications, providing better differentiation of an area of interest.

The tomosynthesis reconstructed slices obtained using high-energy x-rays and a filter, such as the tomosynthesis slice 400B shown in FIG. 4B, may be used in a variety of applications. For example, tomosynthesis reconstructed slices may be used for biopsy guidance, pre-targeting of an area of interest (e.g., area of interest 402 or area of interest 404), targeting of an area of interest, pre-fire or post-fire imaging, etc.

Figures 5A, 5B, 6A, 6B:
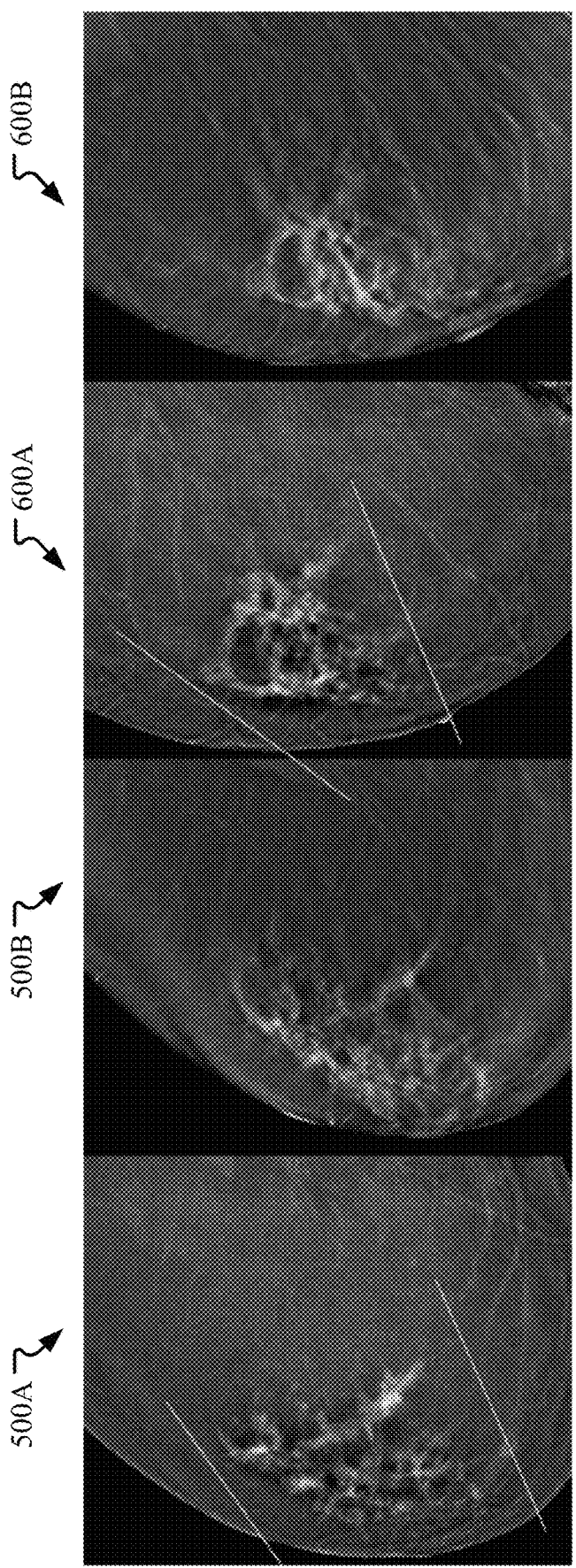
FIG. 5A depicts a Cranial-Caudal (CC) view of a breast generated by subtracting a high energy image and low energy image.
FIG. 5B depicts a CC view of the breast of FIG. 5A generated from a reconstructed slice of tomosynthesis images taken at a high energy through a filter.
FIG. 6A depicts a mediolateral oblique (MLO) view of a breast generated by subtracting a high energy image and low energy image.
FIG. 6B depicts an MLO view of the breast of FIG. 6A generated from a reconstructed slice of tomosynthesis images taken at a high energy through a filter.

FIGS. 5A-5B show CC views of a breast generated using different imaging techniques. Specifically, FIG. 5A depicts a CC view of the breast generated by subtracting a high energy image and low energy image. FIG. 5B depicts a CC view of the breast generated from a reconstructed slice of tomosynthesis images taken at a high energy through a filter. Additionally, FIGS. 6A-6B show MLO views of a breast generated using different imaging techniques. Specifically, FIG. 6A depicts an MLO view of a breast generated by subtracting a high energy image and low energy image. FIG. 6B depicts an MLO view of the breast of FIG. 6A generated from a reconstructed slice of tomosynthesis images taken at a high energy through a filter.

The techniques described herein produce tomosynthesis reconstructed slices that are comparable to other known software-based techniques. For example, in both FIG. 5A and FIG. 6A, the CC tomosynthesis slice 500A and the MLO tomosynthesis slice 600A, each obtained using software-based subtraction of images, show illumination of a contrast agent and calcifications while reducing soft tissue artifacts. Similarly, in both FIG. 5B and FIG. 6B, the CC tomosynthesis slice 500B and the MLO tomosynthesis slice 600B, each obtained using a single tomosynthesis sweep with high-energy x-rays filtered through a copper filter, also show illumination of a contrast agent and calcifications while reducing soft tissue artifacts. Thus, described techniques of filtering x-rays with a filter in a single tomosynthesis sweep to produce tomosynthesis reconstructed slices without software-based subtraction yield results similar to those of software-based subtraction.

Figure 7:
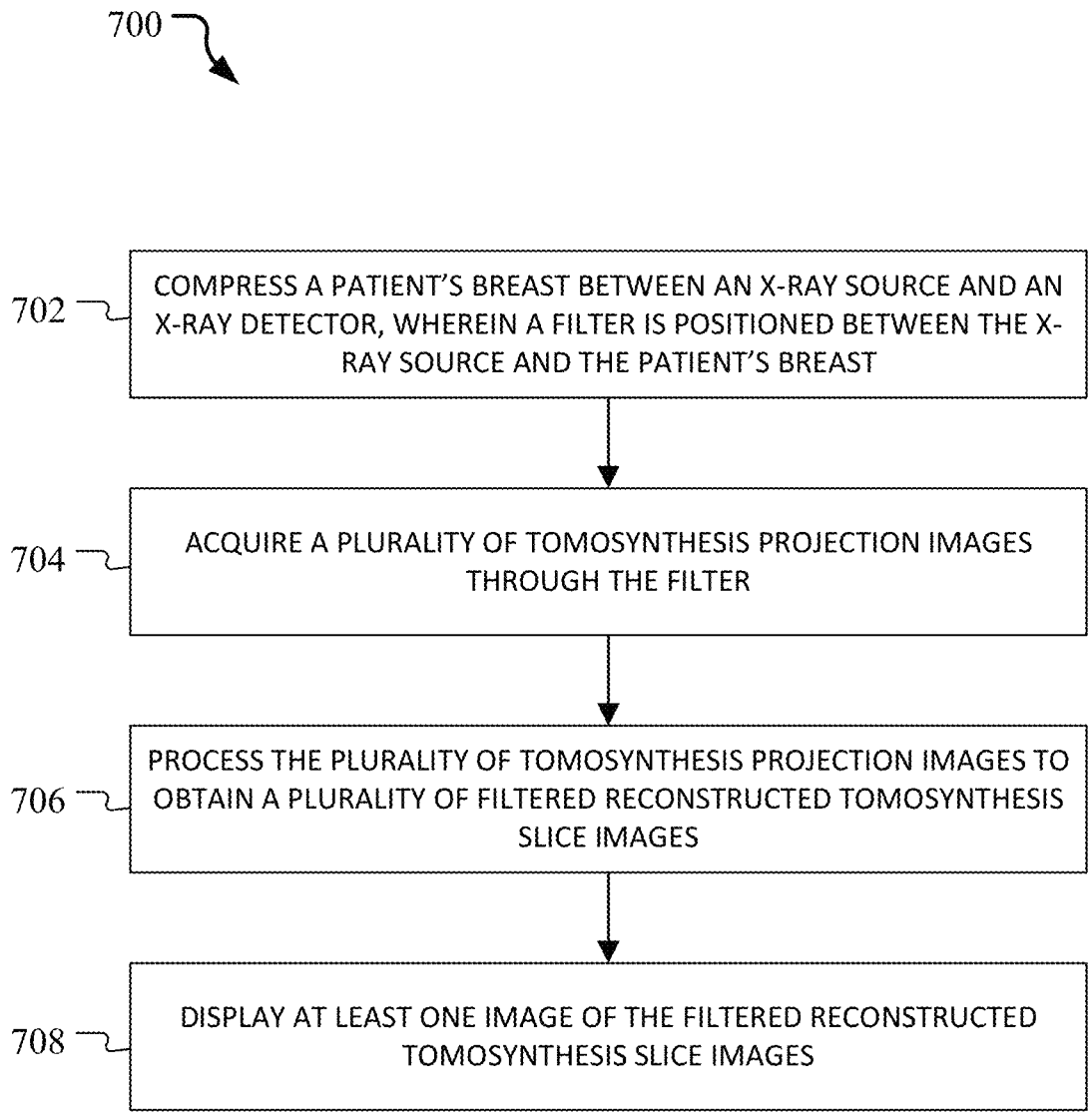
FIG. 7 depicts an example method for contrast-enhanced tomosynthesis with a copper filter.

FIG. 7 depicts an example method for contrast-enhanced tomosynthesis with a copper filter. The operations described with respect to FIG. 7 may be carried out by the systems described herein (e.g., imaging system 100 or by operating environment 800). The method begins at operation 702, where a patient's breast is compressed and positioned between an x-ray source (e.g., x-ray source 122) and an x-ray detector (e.g., x-ray receptor 116). A filter (e.g., filter 170 or filter 200) is positioned between the x-ray source and the patient's breast (e.g., breast 102). Specifically, the filter is positioned such that x-rays generated by the x-ray source flow through the filter prior to traveling through the breast for detection by the x-ray detector. As otherwise described herein, the filter may be composed of a material and may have a thickness. The material and thickness of the filter is associated with a reduction in the quantity of x-rays at a subset of energies of an x-ray beam that pass through the filter. For example, the filter may have a copper material that is 0.3 mm thick. In another example, the filter may have a material and thickness that filters out x-rays below 40 keV or filters out x-rays below 30 keV. In a further example, the filter may not filter out x-rays above 40 keV or above 45 keV.

At operation 704, a plurality of tomosynthesis projection images are acquired through the filter. For example, at each image in the tomosynthesis sweep, the x-rays generated and emitted by the x-ray source are filtered through a physical filter prior to intercepting the breast and prior to detection by the x-ray detector. The plurality of tomosynthesis projection images may be acquired in a single tomosynthesis sweep. The x-ray source may emit an x-ray beam that does not have an energy that is controlled by software. For example, the x-ray beam emitted by the x-ray source to acquire the plurality of tomosynthesis projection images may have a wide spectrum of x-ray energies. The wide spectrum is then filtered by intercepting the physical filter, resulting in a narrower spectrum of x-ray energies. The x-ray beam emitted by the x-ray source may be high energy or low energy or include both high and low energy x-rays.

At the time of acquiring a plurality of tomosynthesis projection images through the filter, the breast may include a contrast agent. The contrast agent may be introduced prior to compression at operation 702. Alternatively, the contrast agent may be introduced to the breast after compression at operation 702 but prior to acquiring the tomosynthesis projection images at operation 704. The tomosynthesis projection images may be acquired after the contrast agent has spread through the breast and prior to substantial dissolution.

At operation 706, the plurality of tomosynthesis projection images are processed to obtain a plurality of filtered reconstructed tomosynthesis slice images. The processing at operation 706 may not use subtraction of other tomosynthesis projection images. For example, the plurality of filtered reconstructed tomosynthesis slice images may be generated only from the plurality of tomosynthesis projection images (e.g., as may be acquired with a single tomosynthesis sweep). At operation 708, at least one image of the filtered reconstructed tomosynthesis slice images is displayed. As further described herein, the displayed image may be used for biopsy guidance, pre-targeting of an area of interest (e.g., area of interest 402 or area of interest 404), targeting of an area of interest, pre-fire or post-fire imaging, etc.

Figure 8:
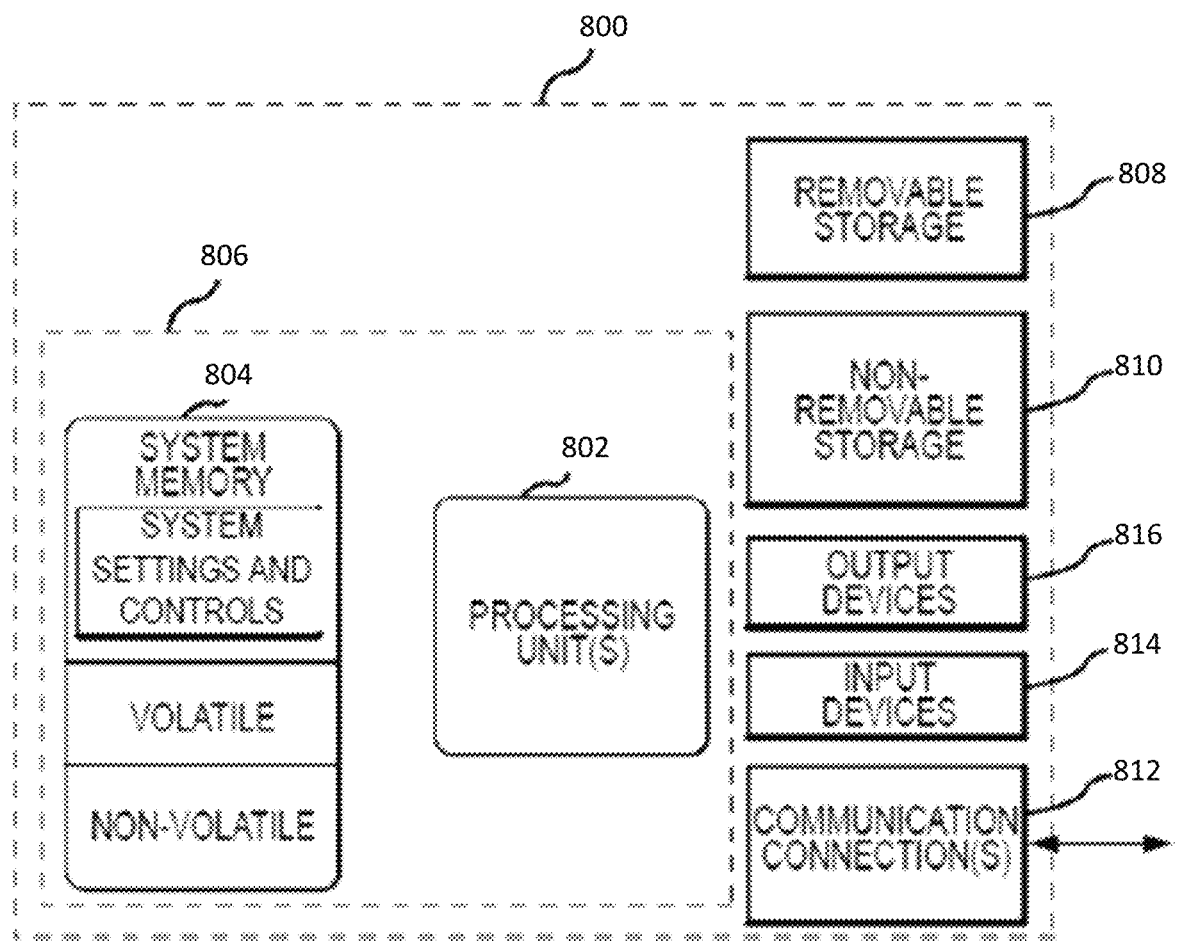
FIG. 8 illustrates an exemplary suitable operating environment for a specimen imaging system.

FIG. 8 illustrates an exemplary suitable operating environment 800 for a specimen imaging system described herein. In its most basic configuration, operating environment 800 typically includes at least one processing unit (or processor) 802 and memory 804. Depending on the exact configuration and type of computing device, memory 804 (storing, instructions to perform projection of an image onto a specimen) may be volatile (such as RAM), non-volatile (such as RAM, flash memory, etc.), or some combination of the two. This most basic configuration is illustrated in FIG. 8 by dashed line 806. Further, environment 800 may also include storage devices (removable, 808, and/or non-removable, 810) including, but not limited to, magnetic or optical disks or tape. Similarly, environment 800 may also have input device(s) 814 such as keyboard, mouse, pen, voice input, etc. and/or output device(s) 816 such as a display, speakers, printer, etc. Also included in the environment may be one or more communication connections 812, such as LAN, WAN, point to point, etc. In embodiments, the connections may be operable to facility point-to-point communications, connection-oriented communications, connectionless communications, etc.

Operating environment 800 typically includes at least some form of computer readable media. Computer readable media can be any available media that can be accessed by one or more processing units (or processors) 802 or other devices comprising the operating environment. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 800 may be a single computer operating in a networked environment using logical connections to one or more remote computers. The remote computer may be a personal computer, a server, a router, a network PC, a peer device or other common network node, and typically includes many or all of the elements described above as well as others not so mentioned. As an example, the operating environment 800 may be shared between one or more imaging systems, such as a breast imaging system and a specimen imaging system (e.g., system 100). As another example, each imaging system (e.g., breast imaging system) may each have a unique operating environment 800. As a further example, the operating environment 800 may be shared between multiple breast imaging system(s) and/or multiple specimen imaging system(s). The logical connections may include any method supported by available communications media. Such networking environments are commonplace in offices, enterprise-wide computer networks, intranets, and the Internet.

Although aspects of the present disclosure are described with respect to image analysis of living breast tissue, it should be appreciated that the present disclosure may also be useful in variety of other applications where identifying different densities of cells may improve image analysis, such as imaging excised breast tissue, other tissue, bone, living organisms, body parts, or any other object, living or dead.

As should be appreciated, while the above methods have been described in a particular order, no such order is inherently necessary for each operation identified in the methods. For instance, the operations identified in the methods may be performed concurrently with other operations or in different orders. In addition, the methods described above may be performed by the systems described herein. For example, a system may have at least one processor and memory storing instructions that, when executed by the at least one processor, cause the system to perform the methods described herein.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art. Further, as used herein and in the claims, the phrase "at least one of element A, element B, or element C" is intended to convey any of: element A, element B, element C, elements A and B, elements A and C, elements B and C, and elements A, B, and C.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method for contrast-enhanced tomosynthesis imaging, the method comprising:
    immobilizing a breast of a patient that has been exposed to a contrast agent, the patient's breast positioned substantially between an x-ray source and an x-ray detector, wherein a filter is positioned between the x-ray source and the patient's breast to proportionally filter a subset of energies of x-ray dose from the x-ray source;
    acquiring, while the patient's breast is immobilized, a plurality of tomosynthesis projection images at a single x-ray energy passing through the filter, and wherein the single x-ray energy includes at least one x-ray energy greater than 33 keV;
    processing the plurality of tomosynthesis projection images without image subtraction to obtain a plurality of filtered reconstructed tomosynthesis slice images; and
    displaying at least one image of the filtered reconstructed tomosynthesis slice images.

2. The method of claim 1, wherein the filter comprises copper.

3. The method of claim 1, wherein the subset of energies of the single x-ray energy proportionally filtered by the filter includes at least one energy below 33 keV.

4. The method of claim 3, wherein the subset of energies of the single x-ray energy proportionally filtered by the filter includes energies below 40 keV.

5. The method of claim 3, wherein the contrast agent has an absorption of the single x-ray energy that is greater for higher energies.

6. An apparatus for contrast-enhanced tomosynthesis imaging, the apparatus comprising:
    an x-ray source capable of selectively moving relative to a patient's breast;
    an imaging x-ray detector;
    a immobilization mechanism for immobilizing the patient's breast, wherein the patient's breast has been exposed to a contrast agent, the immobilization mechanism disposed between the x-ray source and the imaging x-ray detector and comprising a paddle disposed between the breast and the x-ray source and a platform disposed between the breast and the x-ray detector;
    a filter insertable into the apparatus between the x-ray source and the patient's breast, wherein the filter proportionally filters a subset of energies of an x-ray dose emittable by the x-ray source;
    a processor; and
    memory storing instructions that, when executed by the processor, cause the apparatus to perform a set of operations comprising:
        selectively moving the x-ray source through a plurality of selectable positions while emitting a single emission of a single x-ray energy from the x-ray source at each of the plurality of selectable positions;
        detecting, by the x-ray detector, the single emission of the single x-ray energy from the plurality of selectable positions, after the single emission of the single x-ray energy passes through the filter and the patient's breast;
        based on the detected single emission of the single x-ray energy from the plurality of selectable positions, generating, by the processor operatively connected to the x-ray detector, a plurality of tomosynthesis projection images; and
        processing without image subtraction, by the processor, the plurality of tomosynthesis projection images to obtain a plurality of filtered reconstructed tomosynthesis slice images.

7. The system of claim 6, wherein the filter comprises an element with an atomic number of at least 21.

8. The system of claim 7, wherein the filter comprises as sheet member that has a thickness ranging from 0.1 mm to 0.5 mm.

9. The system of claim 8, wherein the sheet member of the filter comprises copper.

10. The system of claim 8, wherein the sheet member is removably secured by an edge member.

* * * * *